(12) United States Patent
Ching et al.

(10) Patent No.: US 7,201,902 B2
(45) Date of Patent: Apr. 10, 2007

(54) **PRODUCTION OF RECOMBINANT PROTEIN PAP 31 FOR THE DIAGNOSIS AND PREVENTION OF *BARTONELLA BACILLIFORMIS* INFECTION**

(75) Inventors: Wei-Mei Ching, Bethesda, MD (US); Laura Hendrix, College Station, TX (US); Jesus Gonzalez, Segovia (ES)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/239,444

(22) Filed: Sep. 23, 2005

(65) Prior Publication Data

US 2006/0067945 A1    Mar. 30, 2006

Related U.S. Application Data

(60) Provisional application No. 60/615,209, filed on Sep. 24, 2004.

(51) Int. Cl.
*A61K 39/12* (2006.01)

(52) U.S. Cl. ................................. 424/186.1; 435/5

(58) Field of Classification Search ............ 424/186.1; 435/5

See application file for complete search history.

(56) References Cited

OTHER PUBLICATIONS

Bowers et al., Gene 206:49-52, 1998.*
Greenspan et al. (Nature Biotechnology 7: 936-937, 1999.*
Klein, Immunology, the Science of Self-Nonself Discrimination, John Wiley & Sons, 1982.*

* cited by examiner

*Primary Examiner*—Robert A. Zeman
*Assistant Examiner*—Brian J. Gangle
(74) *Attorney, Agent, or Firm*—Joseph K. Hemby, Jr.; Albert Churilla

(57) ABSTRACT

The invention relates to a recombinant DNA and polypeptide sequence of an immuno-dominant phage particle associated protein from *Bartonella bacilliformis*. The recombinant protein is easily produced permitting the conduct of more accurate and rapid diagnositic assays for the detection of *B. bacilliformis* infection with reduced reagent and equipment requirements over that required by currently available methods of diagnosis. The DNA and polypeptide sequence is also useful in vaccine preparations against *B. bacilliformis*.

2 Claims, 1 Drawing Sheet

PRODUCTION OF RECOMBINANT PROTEIN PAP 31 FOR THE DIAGNOSIS AND PREVENTION OF *BARTONELLA BACILLIFORMIS* INFECTION

CROSS-REFERENCES TO RELATED APPLICATIONS

This application claims priority to U.S. Provisional application 60/615,209 filed Sep. 24, 2004.

BACKGROUND OF INVENTION

1. Field of Invention

The inventive subject matter relates to a recombinant nucleotide sequence and recombinant protein of *Bartonella bacilliformis* useful for the diagnosis of Oroya fever/verruga peruana due to *Bartonella bacilliformis* infection and for the immunization against *Bartonella bacilliformis* infection.

2. Background Art

*Bartonella bacilliformis*, is a small (0.2–0.5×10 µm), motile, pleomorphic coccobacillus. *B. bacilliformis* is the etiological agent of Oroya fever for the acute phase and verruga peruana for the chronic phase and is endemic in high altitude regions of the Colombian, Ecuadorian and Peruvian Andes. The acute phase is characterized by hemolytic anemia, fever, pallor and transient immuno-suppression (1). The second chronic phase is characterized by cutaneous vascular lesions.

Without antibiotics, mortality rates of 40–88% have been reported (2, 3). However, most of these fatalities are due to secondary infections by *Salmonella* or *Toxoplasma*. Appropriate antibiotic treatment reduces the fatality rate to about 9% (4, 5). Chloramphenicol is an effective treatment for both acute phase bartonellosis and secondary pathogens (4). This antibiotic, however, does not prevent the development of the eruptive phase of the disease. The chronic phase of the disease is best treated with streptomycin, rifampin or ciprofloxacin (4). Regardless of treatment, early diagnosis of the disease is extremely important for effective therapy. Furthermore, despite endemicity in South America, the threat of wide-spread bartonellosis is becoming an increasingly important health issue. Therefore, the disease is also becoming and increasing concern to overseas travelers.

A number of techniques are currently available for the diagnosis bartonella exposure and infection. A summary of these assays are listed in Table 1. Despite the array of available diagnostic methods, they all suffer from either being extremely laborious, expensive or time-consuming. These limitations are especially acute when the required test is conducted by facilities with limited resources or poor laboratory or clinical infrastructure.

Laboratory culture of *B. bacilliformis* is hampered by the bacterium's fastidious nature. Streaking whole blood onto heart-infusion agar plates supplemented with 5% rabbit blood is the best method for isolating the bacteria. Optimum growth is obtained by incubating each specimen at 28° C. without $CO_2$ (4, 6). While highly sensitive, bacterial isolation requires two to five weeks to culture and identify the isolate. However, the prolonged incubation period predisposes the system to contamination and diminishes its

TABLE 1

Current Diagnostic Techniques for Bartonellosis

| Method | Sensitivity | Specificity | Positive Predictive Value | Comment |
|---|---|---|---|---|
| Isolation | | | | Requires 2–5 weeks incubation, special media and techniques (4, 6) |
| Peripheral blood smear | | | | Low sensitivity in the chronic phase; Organisms can be difficult to detect (4, 6, 7, 8) |
| Giemsa thin smear | 36% | 96% | 44% | Low sensitivity; Organisms can be difficult to detect (6) |
| Immunostain | | | | Able to differentiate verruga peruana from bacilliary angiomatosis (8) |
| PCR amplification of 231 bp genomic DNA sequence | | | | (9) |
| PCR amplification of 16S rRNA gene coding region | | | | Able to detect 4 *Bartonella* species (10) |
| PCR amplification of the cell division (ftsZ) gene | | | | Able to distinguish between *B. quintana*, *B. henselae*, and *B. bacilliformis* (11, 12) |
| PCR amplification of the 16S–23S rRNA intergenic region | | | | Able to detect 6 *Bartonella* species (13) |
| PCR assay targeting riboflavin synthase gene (ribC) | | | | Able to detect 6 *Bartonella* species (14) |
| ELISA | | | | Current technique requires expensive technology to prepare antigen (4, 15) |
| Immunoblot with 65 kDa antigen | | | | (16) |
| Immunoblot with Glycine extracted | 30% for acute phase, 94% | 100% | | Not sensitive enough for clinical use; Cross reactions |

TABLE 1-continued

Current Diagnostic Techniques for Bartonellosis

| Method | Sensitivity | Specificity | Positive Predictive Value | Comment |
|---|---|---|---|---|
| antigen | chronic phase | | | with other *Bartonella* species (17) |
| Immunoblot with sonicated antigen | 70% acute phase, 94% chronic phase | 100% | | Cross reactions with other *Bartonella* species (8, 17) |
| Western Blot with FtsZ proteins | | | | Able to distinguish between *B. quintana*, *B. henselae*, and *B. bacilliformis* (11) |
| IFA with irradiated whole-cell antigen | 82% | 92% | 89% | Low sensitivity for the chronic phase(18) | clinical utility when rapid diagnosis is needed or if limited laboratory infrastructure is available.

Peripheral blood smears and histopathologic studies are the most frequently used methods of diagnosis. In the acute phase, peripheral blood smears reveal the intra-erythrocytic bacilli of *B. bacilliformis*. Romanovski, Giemsa, and Wright stains can be used to visualize the bacteria (4, 7). Because the microorganisms are more difficult to visualize in the eruptive phase, final diagnosis is based on histopathological changes and is confirmed by Warthin-Starry staining (7). These staining methods are not desirable because the organisms are often not clearly identifiable, leading to potential misreading and therefore errors in diagnosis. Discrepancies between the interpretation of peripheral blood smears in the regional laboratory and a reference laboratory have been reported (8).

In 1999, Ellis and coworkers determined that Giemsa-stained peripheral smears are not as sensitive as antibody-based methods for the diagnosis of *Bartonella* (6). In this study, peripheral blood smears were stained with Giemsa and examined by light microscopy for the presence of the intra- or extra-erythrocytic coccobaccillary organisms. The sensitivity of this peripheral thin smear procedure was determined to be 36% when compared to bacterial isolation (6). Kosek and coworkers developed an immuno-stain to confirm the presence of *B. bacilliformis* in biopsied skin lesions (8). The biopsy samples were stained by the Steiner and Steiner silver method and then examined immunohistochemically. This immuno-stain method successfully labeled the bacteria in 100% of the lesions previously identified as verruga peruana on the basis of histopathologic appearance. This *B. bacilliformis*-specific immuno-stain can distinguish the miliary form of the verruga peruana from bacillary angiomatosis, a pathologically similar disease (8).

*Bartonella* can be detected and identified directly from clinical samples using PCR-derived assays. In 1992, Maass et al used PCR amplification of a 231 bp genomic *Bartonella* DNA sequence to detect *B. bacilliformis* in blood samples and skin biopsies (8). Matar and coworkers used a PCR method targeting the 16S rRNA gene coding region to detect four species of *Bartonella* (10). Kelly and coworkers designed a PCR-based diagnostic assay based on the cell division protein gene (ftsZ) that can successfully distinguish the genomes of *B. henselae*, *B. quintana*, and *B. bacilliformis* (11). This method requires only one round of PCR while avoiding the problems of specificity and consistency of previous studies. A later study confirmed that the ftsZ gene is a useful tool for detection and identification of *Bartonella* species (12). Jensen and coworkers developed a single-step PCR-based assay targeting the 16S–23S rRNA intergenic region that can detect six species of *Bartonella*, including *B. bacilliformis* (13). Johnson et al developed a genus-specific PCR assay using a single primer pair targeting the riboflavin synthase gene (ribC) able to detect six *Bartonella* species (14). While these molecular techniques offer high sensitivity and specificity, PCR assays require equipment and expertise not widely available in endemic areas.

Serologic assays are also used in the diagnosis of *Bartonella* infections. In 1988, Knobloch developed a *B. bacilliformis*-specific ELISA using liquid chromatography and photodiode array detection for the purification of the antigen (15). This technique requires expensive technology not widely available in endemic areas. In a subsequent study, the ELISA used to test for *B. bacilliformis* was positive in 89% of the culture positive patients (4). ELISAs are useful for large numbers of samples, are relatively inexpensive, and less subjective than other available methods. Additionally, ELISA, with the adequate antigen and assay design, are typically extremely sensitive.

Amano and coworkers used a recombinant *B. bacilliformis* 65 kDa protein in a Western blot in 1997 (16). Mallqui and coworkers developed two immuno-blot preparation methods for the diagnosis of bartonellosis (17). The antigen was prepared by either sonication of the whole cells or glycine extraction. On the basis of high sensitivity and specificity, two diagnostic bands were selected for each preparation method, at 17-kDa and 18-kDa for the sonicated antigen and at 16-kDa and 18-kDa for the glycine extracted antigen. Antibodies to several different bacteria, including *C. psittaci* and *Brucella*, cross-reacted with these *B. bacilliformis* antigens. The high rate of cross-reactivity (40%) with *Brucella* is important because of the similarity between the symptoms of acute phase bartonellosis and Brucellosis. The glycine extraction method is not suitable for use in diagnosis due to its higher rate of cross-reaction and insufficient detection of the acute phase. The immunoblot using the sonicated antigen was 70% sensitive for acute disease, 94% sensitive in identifying chronic bartonellosis and 100% specific. Because it is both highly sensitive and specific, the sonicated immunoblot preparation method is suitable for use in endemic regions. This sonicated-immunoblot preparation method was used in a serological survey after an outbreak of bartonellosis in Peru (8). In 2001, Maguina and coworkers performed ELISA and Western immunoblots (4). The Western immunoblot was positive in 100% of culture-positive patients. All of the patients (n=12) with eruptive phase Bartonellosis had positive ELISA and Western immunoblots.

Kelly and coworkers developed a serological test to distinguish among B. quintana, B. henselae, and B. bacilliformis based on differences in the FtsZ gene (11). Kelly et al synthesized peptides corresponding to the regions of greatest divergence in this gene and injected them into rabbits to generate species-specific antisera. In an immunoblot, the rabbit antisera reacted only with the FtsZ protein from the specific Bartonella species. When the extracts were incubated with antisera to the heterologous peptide sequence, no immunoreactive protein of the size of FtsZ was detected. These results suggest that the differences in these sequences could be used as species-specific antigens for serological diagnosis.

The first successful IFA for the detection of antibodies to B. bacilliformis was developed in 2000(17). The IFA tests uses irradiated whole-cell antigen preparation co-cultivated with Vero cells (18). This IFA test was 82% sensitive in detecting the antibodies in acute-phase blood samples in laboratory-confirmed bartonellosis patients. The IFA was positive for 93% of the convalescent-phase cases (18). The specificity of this IFA is 92%, high enough for epidemiological use. This genus-specific IFA does not react with patient serum with other well-described diseases such as brucellosis, typhoid fever, lyme disease, dengue fever, ehrichiosis, and secondary syphilis. Indirect fluorescence assays are time consuming, costly and require expertise to achieve reproducible results. Serodiagnosis by indirect fluorescence assay is not desirable because of inter-observer variability and the potential for misdiagnosis due to antigen cross-reactivity.

Because B. bacilliformis is the causative agent of Oryoya fever and veruga peruana, where mortality can be exceptionally high, improved methods for B. bacilliformis exposure and infection are needed over existing procedures. Improvements in speed of assay and sensitivity are likely to significantly enhance early diagnosis and therefore administration of treatment with life-saving results. Additionally, a reduction in the required reagents and facilities will expand the ability to conduct the diagnostic methods to facilities with more limited resources, obviating the need to send samples long distances to more complete laboratories for testing thus further improving the speed of diagnostic results.

SUMMARY OF INVENTION

Currently available methods for the diagnosis of B. bacilliformis are inadequate. Therefore, an object of this invention is a DNA construct encoding a 31-kDa major protein from a phage associated protein of B. bacilliformis.

Another object of this invention is a DNA construct encoding a 31-kDa major protein from a phage associated protein from the Peruvian strain of B. bacilliformis.

Another object of this invention is an enzyme-linked immuno-diagnostic method for the detection of B. bacilliformis using all or part of the 31-kDa phage associated protein from B. bacilliformis.

A still further object is the use of the 31-kDa protein from B. bacilliformis in vaccine preparations.

DESCRIPTION OF THE PREFERRED EMBODIMENTS

Figure 1:
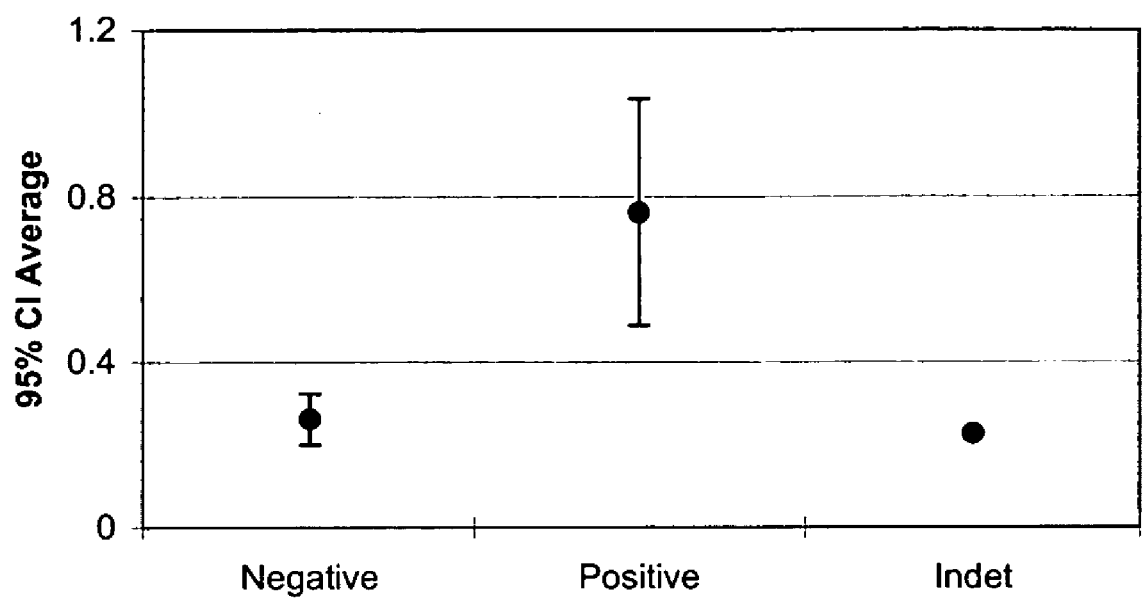
FIG. 1. Enzyme-linked Immunosorbent Assay (ELISA) results patient serum using Pap 31 polypeptide as capture antigen.

We have identified a protein antigen, Pap31, associated with a bacteriophage harbored in Bartonella, spp that is an excellent diagnostic laboratory reagent for the laboratory diagnosis of B. bacilliformis infection. The Pap31 protein, from the virulent Peruvian Strain of B. bacilliformis, is found to be a highly expressed antigen in growing cultures of B. bacilliformis. Furthermore, the protein is immunologically dominant, making it an ideal antigen for use in enzyme-linked immunosorbent assays (ELISA) and in other antibody-based assays. The Pap31 has been sequenced and a recombinant construct produced thereby permitting easy production, in bulk, with high quality control and allowing the reagent to be stored until required for use. Therefore, use of this single protein antigen permits the ELISA and Western blot-based laboratory methods for the diagnosis of B. bacilliformis that are sensitive and more reliable over currently available procedures. Additionally, in addition to its use as a diagnostic reagent, the inventive pap 31 polypeptide reagent is extremely useful either as a subunit vaccine or subunit vaccine component. Furthermore, the pap 31 nucleotide sequence is useful as a component in an anti-B. bacilliformis DNA vaccine.

Identification of Pap 31 as an Immunodominant Protein

The recombinant Pap31 DNA sequence was obtained by SDS-PAGE extraction of the American Type Culture Collection (ATCC) B. bacilliformis strains KC 583 and 584 to form a bacterial cell lysate. Lysate proteins were separated by polyacrylamide gel electrophoresis yielding a dominant protein at approximately 36 kDa for the KC 583 strain and at 31 kDa for the KC 584 strain. DNA from these genes was amplified by polymerase chain reaction (PCR).

Under 2-dimensional (2-D) gel electrophoresis, 4 to 5 moieties migrate near, but not identically to the Pap31 protein. These 2-D spots were easily discriminated by differences in PI and slight differences in relative molecular weight. Pap31 migrated as a band at approximately the same location as the 33–31 kDa molecular weight standard. Strain KC 583 is found to have some repeat units making it slightly larger than the KC 584 strain. N-terminal amino acid sequencing of one spot confirmed the polypeptide as Pap31 based on homology with Pap31 of B. henselae.

In order to obtain B. bacilliformis DNA, PCR primers were designed using the KC 583 and 584 DNA as templates. The PCR products were subsequently cloned into a pCR2.1 vector that was then used to transform Escherichia coli. Plasmid, containing E. coli colonies, were selected and their DNA analyzed and sequenced, using forward and reverse primers from pCR2.1. The DNA sequence of Pap31 determined by this general strategy is as shown in SEQ ID No. 1. The polypeptide sequence is as shown in SEQ ID No. 2.

1-D and 2-D gel electrophoresis of whole B. bacilliformis bacterial lysates shows that Pap31 represents less than 10% of total bacterial protein. However, serum from patients, known to be infected with B. bacilliformis, react strongly to Pap31, compared to total protein staining. Therefore, the recombinant Pap31 polypeptide is an excellent candidate for use as a vaccine or vaccine component against Bartonella infection. The Pap31 DNA construct is also suitable for insertion in an expression system, such as any number of DNA expression vectors or viral vectors, as a DNA vaccine. Expression and purification of the recombinant Pap31 polypeptide can be carried out using any of a number of methods and expression systems, including attaching immuno-reactive tags, such as T7 and His, and purifying the expressed product by affinity chromatography. Purification of expressed protein is best conducted under denaturing conditions using 2M urea.

Pap 31 as Diagnostic Reagent

Because Pap31 is strongly reactive to serum from *B. bacilliformis* patients, the recombinant polypeptide or fragments of it are useful in immuno-assays to detect circulating antibody in serum from these patients. The protein would be well suited for use in any antibody-based assay, including ELISA and rapid antibody-based assays such as immunochromatographic assays. The recombinant polypeptide is also useful for use in confirmatory Western blot analysis. Use of these methods, verses that currently employed for *B. bacilliformis*, This obviates the need for specific detection of bacteria or bacterial proteins greatly enhancing speed of diagnosis and reducing the required infrastructure to support currently available diagnostic methods.

EXAMPLE 1

Use of Pap31 in Antibody-based Detection Assays

Currently available methods for the diagnosis of *B. bacilliformis* are time consuming and require significant infrastructural support. In addition to bacterial isolation and culture from patient samples, the gold-standard immunoassay currently available for the detection of *B. bacilliformis* infection is by indirect fluorescence assay (IFA). This assay, however, is often not sensitive and can lead to inaccurate results. The assay is also relatively labor and reagent intensive.

A typical IFA assay for *Bartonella* diagnosis is conducted by a series of relatively laborious steps including producing *B. bacilliformis* (antigen) by growing the bacteria in Vero cell cultures. The antigen is then harvested and irradiated in order to render the material safe. The antigen is drawn up using a hematocrit tube and the material dotted onto to 12-well slides. Twenty-five (19) microliter dilutions of serum samples, diluted in skim milk diluent, are added to the rows of antigen and incubated for 30 minutes, washed with phosphate buffered saline (PBS) and let air-dry. To each well, 25 μl of diluted anti-human fluorescently-labeled antibody is added and incubated at 37° C. for 30 minutes, washed with PBS and let air-dry. Using a glycerol mounting medium, slides are covered and read within 12 hours under a fluorescent microscope.

ELISA significantly reduces the labor and time required for IFA diagnosis. Use of recombinant Pap31 in ELISA diagnostec assays is accomplished essentially as follows:

1. Microtiter plates with 96 wells were coated with 0.3 μg/well of Pap31 and stored in 4° C. for 2 days.
2. Plates are washed ×3 with wash buffer (0.1% TWEEN™-20 (polyoxyethylene sorbitan) in PBS).
3. Plates are blocked with 200 μl/well of blocking buffer (5% skim milk in wash buffer) ×45 minutes and then rinsed three times.
4. Sera is diluted in blocking buffer and 100 μl/well is added and incubated ×2 hours.
5. Plates are washed three times with wash buffer.
6. Plates are then incubated with 100 μl/well of enzyme-labeled (e.g. peroxidase) anti-human immunoglobulin for 1 hour.
7. The plates are washed three times with wash buffer.
8. Substrate is added to the wells and reas after 15 to 30 minutes.

A standard curve is constructed in conjunction with the above ELISA procedure following exposure of the Pap31 bound plates to a range of concentrations of a known Pap31-specific antibody. The extent of measured binding of patient serum antibody is compared to a graphic representation of the binding of the Pap31-specific antibody concentrations.

An example of ELISA results is shown in FIG. 1. In FIG. 1, mean and 95% confidence interval (CI) of ELISA optical density (OD) is grouped by IFA results. For the IFA results shown in FIG. 1, sera with titers greater than 256 were designated as positive. Samples labeled as Indetermined are those where the sample could not be scored as positive or negative even after repeated testing up to five times by IFA. As shown in FIG. 1, of the 137 samples tested, 107 were IFA negataive, 29 were IFA positive and one was indetermined. The ELISA optical density range (95% confidence interval (CI)) of the IFA negative samples did not overlap with those of positive IFA samples. The results show that the Pap31 reagent incorporated ELISA was both highly sensitivity and specific. Because the recombinant Pap31 is easy to purify, store and able to survive multiple rounds of freeze-thawing cycles without a loss of antigenicity, antibody-based assays using recombinant Pap31 will yield more reproducible diagnostic results compared to purified antigen.

The inventive polypeptide sequence can also be utilized as capture antigen in rapid antibody-based assays including immunochromographic assays (20) or other biosensors utilizing metal matrixes (21, 22). Pap 31 polypeptide is spotted onto a solid matrix strips, such as nitrocellulose. Serum from suspected bartonella infected patients is then applied to pads containing anti-human antibody conjugated with colloidal gold or other indicator. The anti-*bartonella*/anti-human colloidal gold complex migrates up the strip until captured by the *bartonella* polypeptides. Visualization is then made detection of a color change. In assays using metal matrixes for ligand attachment, pap 31 polypeptide as capture antigen is bound to chips or wafers composed of metal thin-films such as silicone. Patient serum applied to the chips is then captured by the pap 31 polypeptide. Bound antibody is visualized by exposing the serum-exposed chips/wafers to secondary antibody probes.

EXAMPLE 2

Pap 31 in Western Blot Confirmatory Analysis

Western blot analysis is conducted essentially as follow:

1. After SDS-PAGE separation of Pap31, the protein is transferrfed to a solid substrate, such as PVDF membrane (e.g. 0.45 μm pore size) or nitrocellose in a buffer consisting of 0.25 M RIS™ (tris(Pentafluorophenyl) borane), 0.192 M Glycine and 20% (vol/vol) methanol for 1 hour at 400 mA.
2. Unreacted sites are blocked with 5% milk in Tris-borate-saline (TBS) with 0.2% TWEEN™-20 (polyoxyethylene sorbitan) overnight.
3. The membrane is washed twice for 5 minutes each in TBS-Tween.
4. The membrane is then cut into strips. Each strip is incubated wit a single primary antibody (sera) diluted in 5% (mass/vol) milk powder in TBS-TWEEN™ (polyoxyethylene sorbitan) for 1 hour.

5. Unbound serum are removed by rinsing twice with TBS-TWEEN™ (polyoxyethylene sorbitan) followed by three rounds of agitation in TBS-Tween for five minutes each.
6. The strips are then incubated with enzyme-labeled anti-human antibody (e.g. goat anti-human IgG) diluted in 5% milk powder in TBS-TWEEN (polyoxyetylene sorbitan) for 1 hour on an orbital shaker.
7. Unbound secondary antibody is removed with two rinses in TBS-TWEEN™ (polyoxyethylene sorbitan) and three successive washes by agitation in TBS-TWEEN™ (polyoxyethylene sorbitan) for 5 minutes followed by distilled water.
8. The strips are exposed to substrate and the antibody binding is measured.

The assay can be carried out with a strip being used for each serum sample to be tested. A standard curve can be made by conducting the above Western blotting procedure following exposure of Pap31 bound strips to a range of concentrations of a known Pap31-specific antibody. The extent of measured binding of patient serum antibody is compared to a graphic representation of the binding of the Pap31-specific antibody concentrations that is measured by a number of methods including densitometry.

REFERENCES

1) Groot H, 1951. Human bartonellosis or Carrion's disease. Gradwohl R B H, Benitez-Soto L. Felsenfeld O, eds. *Clinical Topical Medicine*. St. Louis, Mo.: Mosby Publishing Co., 615–640.
(2) Kelly T. M., Padmalayam I, Baumstark B. R. Use of the cell division protein FtsZ as a means of differentiating among *Bartonella* species. *Clin Diagn Lab Immunol.* 1998 November, 5(6):766–72.
(3) Gray G. C., Johnson A. A., Thorton S. A., et al. An epidemic of Oroya fever in the Peruvian Andes. *Am J Trop Med Hyg* 1990; 42:215–21.
(4) Maguina, C. Garcia, P. J., Gotuzzo, E, Cordero, L, Spach, D. H. Bartonellosis (Carrion's Disease) in the Modern Era. *Clin Infect. Dis.* 2001:33 (15 September).
(5) Maguiñia-Vargas, C., H. Lumbreras, E. Gotuzzo, E. Crosby, and J. Irrivaren. 1988. Clinical and laboratory study of patients with acute phase of Carrión's disease in the Hospital Base Cayetano Heredia between 1969–1987. Publication 63. International Congress for Infectious Diseases, Rio de Janeiro, Brazil.
(6) Ellis B A, Rotz L D, Leake J A, Samalvides F, Bernable J, Ventura G, Padilla C, Villaseca P, Beati L, Regnery R, Childs J E, Olson J G, Carrillo C P. An outbreak of acute bartonellosis (Oroya fever) in the Urubamba region of Peru, 1998. *Am J Trop Med Hyg.* August 1999, 61(2): 344–9.
(7) Maco, V., Maguiña, C., Tirado, A. et al. Carrion's disease (*Bartonellosis bacilliformis*) confirmed by histopathology in the High Forest of Peru. *Rev. Inst. Med. trop. S. Paulo*, May/June 2004, vol. 46, no. 3, p. 171–174.
8) Kosek M, Lavarello R, Gilman R H, Delgado J, Maguina C, Verastegui M, Lescano A G, Mallqui V, Kosek J C, Recavarren S, Cabrera L. Natural history of infection with *Bartonella bacilliformis* in a nonendemic population. *J Infect Dis.* September 2000, 182(3):865–72.
(9) Maass M, Schreiber M, Knobloch J. Detection of *Bartonella bacilliformis* in cultures, blood, and formalin preserved skin biopsies by use of the polymerase chain reaction. *Trop Med Parasitol. September* 1992, 43(3): 191–4.
(10) Matar, G. M., B. Swaminathan, S. B. Hunter, L. N. Slater, and D. F. Welch. 1993. Polymerase chain reaction-based restriction fragment length polymorphism analysis of a fragment of the ribosomal operon from *Rochalimae* species for subtyping. J. Clin. Microbiol. 31:1739–1734.
(11) Kelly T. M., Padmalayam I, Baumstark B. R. Use of the cell division protein FtsZ as a means of differentiating among *Bartonella* species. *Clin Diagn Lab Immunol.* November 1998, 5(6):766–72.
(12) Zeaiter Z, Liang Z, Raoult D. Genetic classification and differentiation of *Bartonella* species based on comparison of partial ftsZ gene sequences. *J Clin Microbiol. October* 2002; 40(10):3641–7.
(13) Jensen, W. A., M. Z. Fall, J. Rooney, D. L. Kordick, and E. B. Breitschwerdt. 2000. Rapid Identification and Differentiation of *Bartonella* Species Using a Single-Step PCR Assay. J. Clin. Microbiol. 38 (5): 1717–1722.
(14) Johnson G., M. Ayers, S. C. C. McClure, S. E. Richardson, and R. Tellier. 2003. Detection and Identification of *Bartonella* species Pathogenic for Humans by PCR amplification Targeting the Riboflavin Synthase Gene (ribC). J. Clin. Micro. 41 (March 2003) 1069–1072.
(15) Knobloch, J. 1988. Analysis and preparation of *Bartonella bacilliformis* antigens. *Am. J. Trop. Med. Hyg.* 39:173–178.
(16) Amano Y, Rumbea J, Knobloch J, Olson J, Kron M. Bartonellosis in Ecuador: serosurvey and current status of cutaneous verrucous disease. *Am J Trop Med Hyg. August* 1997, 57(2):174–9.
(17) Mallqui, V., Speelmon, E. C., Verastegui, M., Maguina-Vargas, C., Pinell-Salles, P., Lavarello, R., Delgado, J., Kosek, M., Romero, S., Arana, Y., Gilman, R. H. January 2000 7(1):1–5.
(18) Chamberlin J, Laughlin L, et al. Serodiagnosis of *Bartonella bacilliformis* infection by indirect fluorescence antibody assay: test development and application to a population in an area of bartonellosis endemicity. *J Clin Microbiol.* 2000 November, 38(11):4269–71.
(19) Chamberlin J, Laughlin L, Romero S, Solorzano N, Gordon S, Andre R, Pachas P, Friedman H, Ponce C, Watts D. Epidemiology of endemic *Bartonella bacilliformis*: a prospective cohort study in a peruvian mountain valley community. JID 2002; 186:983–90.
(20) Burans, J., A. Keleher, T. O'Brien, J. Hager, A. Plummer and C. Morgan. 1996. Rapid method for the diagnosis of *Bacillus anthracis* infection in clinical samples using a hand-held assay. Salisbury Med. Bull., 87 (Special Suppl) 36.
(21) Jenison, R., S. Yang, A. Haeberli and B. Polisky. 2001. Interference-based detection of nucleic acid targets on optically-coated silicon. Nature Biotechnol. 19, 62.
(22) Jenison, R., H. La, A. Haeberli, R. Ostroff and B. Polisky. 2001. Silicon-based biosensors for rapid detection of protein or nucleic acid targets. Clin. Chem. 47, 1894.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. An isolated, immunogenic Pap31 polypeptide of a *Bartonella bacilliformis* bacteriophage, wherein said polypeptide consists of the sequence set forth in SEQ ID NO:2.

2. The polypeptide of claim 1, wherein said polypeptide is encoded by a polynucleotide with a sequence consisting of SEQ ID NO:1.

* * * * *

SEQUENCE LISTING

<160> NUMBER OF SEQ ID NOS: 2

<210> SEQ ID NO 1
<211> LENGTH: 825
<212> TYPE: DNA
<213> ORGANISM: Bartonella bacilliformis

<400> SEQUENCE: 1

```
atgatcccgc aagaaatatc accgattatt tctgctccta ctttctcgtg gacaggtctt      60
taccttggtg gtcaaattgg tggtctttca ggtaaacatg actttaaagc tattggtaaa     120
gattcagaat ggccttttgc aaataaagat ctgaaagttt caggttttgt aggtggtttg     180
tacgcaggtt ctaatattga tctcggcagt ggccttgtct tgggtgttga tacagatatt     240
gtttggttg ataaggaagg taaattatct tccaaccaca aggcagagac tcaagatgat      300
gcagatgctt tcaagcagat ttttgacgag aataagattg aggtcgctaa gggccaaatt     360
aaggaactta cacagaattt ttctcttaaa gaaagtgggg ctggtgccac acgggtacgc     420
atcggttttg tgctgaccg tattatgcct tatgtctcag ggggtgttgc ttacacgcag      480
gtacaagcta ttggttcagc tatcttaaaa ggcacgaaag atactggtac tgaaggcggt     540
ggcggtactg aaggcggtgg cggtactgaa ggcggtggcg tagtgctag caaagcagta     600
cgttcagaag cgcttgatgt acttgcttct ggcactataa ccgatgagaa aaagacactg     660
cttggttata cccttggtgc tggtgttgat tttgcaatga ccgacaatgt tattctgcgt     720
acagagtatc gttactctga ttttggcaaa aagaaatttg taaaagacgc gatcgaaaca     780
aactacaaaa ccaatgattt ccgtgttggt gttgcgtaaa aattc                      825
```

<210> SEQ ID NO 2
<211> LENGTH: 271
<212> TYPE: PRT
<213> ORGANISM: Bartonella bacilliformis

<400> SEQUENCE: 2

```
Ile Pro Gln Glu Ile Ser Pro Ile Ile Ser Ala Pro Thr Phe Ser Trp
1               5                   10                  15

Thr Gly Leu Tyr Leu Gly Gly Gln Ile Gly Gly Leu Ser Gly Lys His
            20                  25                  30

Asp Phe Lys Ala Ile Gly Lys Asp Ser Glu Trp Pro Phe Ala Asn Lys
        35                  40                  45

Asp Leu Lys Val Ser Gly Phe Val Gly Gly Leu Tyr Ala Gly Ser Asn
    50                  55                  60

Ile Asp Leu Gly Ser Gly Leu Val Leu Gly Val Asp Thr Asp Ile Val
65                  70                  75                  80

Trp Val Asp Lys Glu Gly Lys Leu Ser Ser Asn His Lys Ala Glu Thr
                85                  90                  95

Gln Asp Asp Ala Asp Ala Phe Lys Gln Ile Phe Asp Glu Asn Lys Ile
            100                 105                 110

Glu Val Ala Lys Gly Gln Ile Lys Glu Leu Thr Gln Asn Phe Ser Leu
        115                 120                 125

Lys Glu Lys Trp Ala Gly Ala Thr Arg Val Arg Ile Gly Phe Gly Ala
    130                 135                 140

Asp Arg Ile Met Pro Tyr Val Ser Gly Gly Val Ala Tyr Thr Gln Val
145                 150                 155                 160
```

-continued

```
Gln Ala Ile Gly Ser Ala Ile Leu Lys Gly Thr Lys Asp Thr Gly Thr
                165                 170                 175

Glu Gly Gly Gly Gly Thr Glu Gly Gly Gly Gly Thr Glu Gly Gly Gly
            180                 185                 190

Gly Ser Ala Ser Lys Ala Val Arg Ser Glu Ala Leu Asp Val Leu Ala
        195                 200                 205

Ser Gly Thr Ile Thr Asp Glu Lys Lys Thr Leu Leu Gly Tyr Thr Leu
    210                 215                 220

Gly Ala Gly Val Asp Phe Ala Met Thr Asp Asn Val Ile Leu Arg Thr
225                 230                 235                 240

Glu Tyr Arg Tyr Ser Asp Phe Gly Lys Lys Lys Phe Val Lys Asp Ala
                245                 250                 255

Ile Glu Thr Asn Tyr Lys Thr Asn Asp Phe Arg Val Gly Val Ala
            260                 265                 270
```